United States Patent [19]

Miller

[11] Patent Number: 5,108,741
[45] Date of Patent: Apr. 28, 1992

[54] ANTI-FUNGAL TREATMENT METHOD USING POLYETHYLENE OXIDE POWDER

[76] Inventor: David F. Miller, 2351 Edith Ave., Burlington, Ontario, L7R 1N4, Canada

[21] Appl. No.: 603,291
[22] Filed: Oct. 25, 1990
[51] Int. Cl.⁵ ............................................. A61K 31/74
[52] U.S. Cl. .................................. 424/78.38; 514/858
[58] Field of Search ........................... 514/858; 424/78

[56] References Cited

U.S. PATENT DOCUMENTS 4,136,172 1/1979 Walliczek .......................... 424/632
4,465,663 8/1984 Schmolka .................. 424/DIG. 10

FOREIGN PATENT DOCUMENTS 5535025 3/1980 Japan .

Primary Examiner—Thurman K. Page
Assistant Examiner—Peter F. Kulkosky
Attorney, Agent, or Firm—Burke-Robertson

[57] ABSTRACT

There is provided a new and useful method for the treatment of fungal infections comprising applying to the infected area a composition containing from 0.5 to 100% of an ethylene oxide polymer.

7 Claims, No Drawings

ANTI-FUNGAL TREATMENT METHOD USING POLYETHYLENE OXIDE POWDER

FIELD OF THE INVENTION

This invention relates to methods of treatment for fungal infections.

BACKGROUND OF THE INVENTION

There has long been a need for an effective means of eliminating fungal infections. While such infections attack many external sites on the body, a very common such area is that around the toes. This results in the commonly known problem of athlete's foot.

While numerous products have been available for combating such fungal infections as athlete's foot, these have been of varying levels of effectiveness. Some products appear to work for some people and not for others and for some types of infections and not for others. As a result, certain fungal infections tend to remain for extended periods of time, stubbornly resisting elimination by existing products.

As is known by those who have suffered from these problems, they are normally accompanied by a severe itching in the affected area.

There has thus been a long standing need for an improved method of elimination of these fungal infections.

Against this background the present invention provides an improved method for treating and in many cases eliminating fungal infections.

PRIOR ART

Applicant has extensively reviewed available information relative to methods of treating fungal infections, and no method has come to Applicant's attention, which is comparable to that of the present invention.

The product which forms the active ingredient for use in the present method is known and was patented for other purposes. Thus, U.S. Pat. 2,978,812, issued Apr. 11, 1961, to Block Drug Company, Inc., pertains to an improved artificial denture having a securing surface carrying a fixative comprising in part ethylene oxide polymers.

BRIEF DESCRIPTION OF THE INVENTION

A method has now been devised for treatment of fungal infections which utilizes ethylene oxide polymers as active ingredient in a composition to be applied to infected areas. Thus, the invention provides a method for the treatment of fungal infections comprising applying to the infected area a composition containing from 0.5 to 100% of an ethylene oxide polymer.

In a preferred embodiment the ethylene oxide polymers are present in an amount of about 5%.

DETAILED DESCRIPTION OF THE PREFERRED EMBODIMENTS

Ethylene oxide is a highly dangerous and most disagreeable compound. It is, however, useful and is used under carefully controlled conditions as a disinfectant. It is felt that this very lethal disinfecting property of the monomer persists in certain ways in the polymer and thus provides the efficacy of the present invention.

In the high molecular weight polymers of ethylene oxide, say in the range of 500,000 to 5,000,000 molecular weight, the product is non-toxic and non-irritating to human tissue. Furthermore, the polymers can readily be formed into free-flowing and non-caking powders.

The powders may include fillers, extenders, plasticizers, flow promoters and the like substances.

The basic method comprises the application of ethylene oxide polymers, preferably in powdered form, to the site of a fungal infection. Once applied, the composition is preferably left in place for a period ranging from one half hour to several hours, usually not exceeding four hours. The composition is then preferably washed from the site. If symptoms at this point persist as, for example, in continued itching, the procedure is repeated.

It has been found that one application is frequently sufficient to eliminate the infection. Testing to date has shown that rarely will more than three or four applications be required.

EXAMPLE 1

In all of the examples the composition was applied in powder form. A composition containing about 5% ethylene oxide polymers and about 95% fillers, extenders and the like was applied to the area between the toes of a subject who was suffering from a stubborn case of athlete's foot. The composition was left in place for a period of about one hour. After about the first one half hour the major symptom, severe itching, had disappeared. The composition was washed from the infected area after about one hour, and it was noted that the itching sensation did not return.

The treatment was repeated once per day for the following three days. The infection at that point had apparently been eliminated.

EXAMPLE 2

A composition comprising 5% ethylene oxide polymers and about 95% fillers, extenders and the like was applied to an area between the toes of a subject who was suffering from athlete's foot. The characteristic itching rapidly disappeared, and the composition was then washed off.

About one day later the fungal infection had reappeared and extended to slightly different areas. It was concluded that the composition had not been applied over the entirety of the infected area. The composition was reapplied for about an eight hour period, subsequently washed off and reapplied for a second eight hour period.

Following this treatment the infection had apparently been eliminated.

EXAMPLE 3

A composition comprising about 5% ethylene oxide polymers and about 95% fillers, extenders and the like was applied to infected areas of a subject suffering from athlete's foot. The application was made twice at four hour intervals.

Following the second application the infection apparently had been eliminated.

Testing in general established that most cases of athlete's foot can be substantially eliminated by the method described utilizing a single application of the composition to the infected area.

What I claim as my invention:

1. A method for the treatment of fungal infections comprising applying to the infected area a composition in powder form containing about 5% ethylene oxide polymer having a molecular weight in the range 500,000 to 5,000,000, wherein said polymer is the sole active ingredient.

2. A method for the treatment of fungal infections of the skin comprising applying to the infected area a composition in powder form containing about 5% ethylene oxide polymer having a molecular weight in the range 500,000 to 5,000,000, wherein said polymer is the sole active ingredient.

3. A method for the treatment of athlete's foot comprising applying to the infected area a composition in powder form containing about 5% ethylene oxide polymer having a molecular weight in the range 500,000 to 5,000,000, wherein said polymer is the sole active ingredient.

4. The method of any one of claims 1, 2 or 3 comprising applying said composition in powder form to said infected area, allowing said composition to remain in place on said infected area for a period up to eight hours, and then washing said composition from said infected area.

5. The method of any one of claims 1, 2 or 3 comprising applying said composition in powder form to said infected area, allowing said composition to remain in place on said infected area for a period up to four hours, and then washing said composition from infected area.

6. The method of any one of claims 1, 2 or 3 comprising applying said composition in powder form to said infected area, allowing said composition to remain in place on said infected area for a period up to four hours, and then washing said composition from said infected area; and repeating the foregoing procedure until said infection has been eliminated.

7. The method of any one of claims 1, 2 or 3 wherein said composition contains at least one of fillers, extenders, plasticizers, and flow promoters.

* * * * *